United States Patent [19]

Lake et al.

[11] Patent Number: 5,506,132
[45] Date of Patent: Apr. 9, 1996

[54] HUMAN ANTIBODIES AGAINST VARICELLA-ZOSTER VIRUS

[75] Inventors: Philip Lake, Parsippany, N.J.; Lars Ostberg, Los Altos, Calif.

[73] Assignee: Sandoz Pharmaceuticals Corporation, East Hanover, N.J.

[21] Appl. No.: 217,918

[22] Filed: Mar. 24, 1994

Related U.S. Application Data

[63] Continuation-in-part of Ser. No. 98,479, Jul. 28, 1993, abandoned.

[51] Int. Cl.$^6$ .............................. C12N 5/10; C07K 16/08; C07H 15/12
[52] U.S. Cl. ................................ 435/240.2; 435/240.27; 435/320.1; 530/387.3; 530/388.15; 530/388.3; 536/23.53
[58] Field of Search .......................... 435/240.27, 240.2, 435/320.1; 530/387.3, 388.15, 388.3; 536/23.53; 424/142.1

[56] References Cited

FOREIGN PATENT DOCUMENTS 0481089  4/1992  European Pat. Off. .

OTHER PUBLICATIONS

Sugano et al., Eur. J. Immunol., 17:359–64, 1987.
Ostberg et al., Hybridoma 2:361–367, 1983.
Morrison, Science 229:1202–1207, 1985.
Waldmann, Science 252:1657–1662, 1991.
Casale et al. Science 234:476–79, 1986.

*Primary Examiner*—Paula K. Hutzell
*Attorney, Agent, or Firm*—Townsend and Townsend and Crew

[57] ABSTRACT

The invention provides human monoclonal antibodies specific for the glycoprotein II subunit of Varicella-zoster virus. Preferred antibodies exhibit strong complement-independent neutralizing activity, antibody dependent cellular cytotoxicity, and cross-reactivity with multiple strains of Varicella-zoster virus.

16 Claims, 5 Drawing Sheets

```
ATG GAC ATG AGG GTC CCC GCT CAG CTC GGG CTC CTG CTG TGG CTC CCA GGT GCC
 M   D   M   R   V   P   A   Q   L   G   L   L   L   W   L   P   G   A

AAA TGT GAC ATC CAG ATG ACC CAG TCT CCT TCC ACC CTG TCT GCA GTA GGA GAC AGA
 K   C   D   I   Q   M   T   Q   S   P   S   T   L   S   A   V   G   D   R

GTC ACC ATC ACT TGC CGG GCC AGT CAG AGT ATT AGT AGT TGG TTA GCT TAT CAG CAG
 V   T   I   T   C   R   A   S   Q   S   I   S   S   W   L   A   Y   Q   Q

ACA CCA CGG AAA GCC CCT AAA CTC ATG ATC TAT AAG GCG TCT ATT TTA GAA AAT GGG
 T   P   R   K   A   P   K   L   M   I   Y   K   A   S   I   L   E   N   G

CCA TCA AGG TTC AGC GGC AGT GGA TCT GGG ACA GAA TTC ACT CTC ACC ATC AGC AGC
 P   S   R   F   S   G   S   G   S   G   T   E   F   T   L   T   I   S   S

CAG CCT GAA GAT TTT GCA ACT TAT TAC TGT CAA CAG TAT TAT AGT TAT CCC TGG ACG TTC
 Q   P   E   D   F   A   T   Y   Y   C   Q   Q   Y   Y   S   Y   P   W   T   F

GGC CAA GGG ACC AAG GTG GAA ATC AAA
 G   Q   G   T   K   V   E   I   K
```

FIG. 4A

| ATG | GAC | TGG | ACC | TGG | AGG | TTC | CTC | TTT | GTG | GTG | GCA | GCT | ACA | GGT | GTC | CTG | TCC | CAG |
|---|---|---|---|---|---|---|---|---|---|---|---|---|---|---|---|---|---|---|
| M | D | W | T | W | R | F | L | F | V | V | A | A | T | G | V | L | S | Q |
| GTG | CAG | TTG | GTG | CAG | TCT | GGG | GCT | GAG | GTG | AAG | AAG | CCT | GGG | TCC | TCG | GTC | AAG | GTC | TCC |
| V | Q | L | V | Q | S | G | A | E | V | K | K | P | G | S | S | V | K | V | S |
| TGC | AAG | GCT | TCT | GGA | GGC | ACC | TTC | AGC | AGC | TAT | GCT | ATC | AGC | TGG | GTG | CGA | CAG | GCC | CCT |
| C | K | A | S | G | G | T | F | S | S | Y | A | I | S | W | V | R | Q | A | P |
| GGA | CAA | GGG | CTT | GAG | TGG | ATG | GGA | CGC | ATC | ATG | CCT | CTC | TTT | GGT | ACG | ACC | TCC | TAC | GCA |
| G | Q | G | L | E | W | M | G | R | I | M | P | L | F | G | T | T | S | Y | A |
| CAG | AAG | TTC | CAG | GGC | AGA | GTC | ACG | ATT | AGC | GCG | GAC | TCT | ACG | AGC | ACA | GCC | TAC | ATG |
| Q | K | F | Q | G | R | V | T | I | S | A | D | S | T | S | T | A | Y | M |
| GAG | CTG | AGC | AGC | CTG | AGA | TCT | GAC | GAC | ACG | GCC | ATG | TAT | TAC | TGT | GCG | AGA | GAC | ATA | ACA |
| E | L | S | S | L | R | S | D | D | T | A | M | Y | Y | C | A | R | D | I | T |
| GCA | CCT | GGA | GCC | GCA | CCC | CTG | AAT | TTC | TAC | GGC | ATG | GAC | GTC | TGG | GGC | CAA | GGG |
| A | P | G | A | A | P | L | N | F | Y | G | M | D | V | W | G | Q | G |
| ACC | ACG | GTC | ACC | GTC | TCC | TCA |
| T | T | V | T | V | S | S |

FIG. 4B

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
      ( A ) LENGTH: 387 base pairs
      ( B ) TYPE: nucleic acid
      ( C ) STRANDEDNESS: single
      ( D ) TOPOLOGY: linear ( i i ) MOLECULE TYPE: cDNA ( i i i ) HYPOTHETICAL: NO ( i v ) ANTI-SENSE: NO ( i x ) FEATURE:
      ( A ) NAME/KEY: CDS
      ( B ) LOCATION: 1..387

( x i ) SEQUENCE DESCRIPTION: SEQ ID NO:1:

| | | | | | | | | | | | | | | | | |
|---|---|---|---|---|---|---|---|---|---|---|---|---|---|---|---|---|
| ATG | GAC | ATG | AGG | GTC | CCC | GCT | CAG | CTC | CTG | GGG | CTC | CTG | CTG | CTC | TGG | 48 |
| Met | Asp | Met | Arg | Val | Pro | Ala | Gln | Leu | Leu | Gly | Leu | Leu | Leu | Leu | Trp | |
| 1 | | | | 5 | | | | | 10 | | | | | 15 | | |
| CTC | CCA | GGT | GCC | AAA | TGT | GAC | ATC | CAG | ATG | ACC | CAG | TCT | CCT | TCC | ACC | 96 |
| Leu | Pro | Gly | Ala | Lys | Cys | Asp | Ile | Gln | Met | Thr | Gln | Ser | Pro | Ser | Thr | |
| | | | 20 | | | | | 25 | | | | | 30 | | | |
| CTG | TCT | GCA | TCT | GTA | GGA | GAC | AGA | GTC | ACC | ATC | ACT | TGC | CGG | GCC | AGT | 144 |
| Leu | Ser | Ala | Ser | Val | Gly | Asp | Arg | Val | Thr | Ile | Thr | Cys | Arg | Ala | Ser | |
| | | | 35 | | | | 40 | | | | | 45 | | | | |
| CAG | ACT | ATT | AGT | ACC | TGG | TTG | GCC | TGG | TAT | CAG | CAG | ACA | CCA | CGG | AAA | 192 |
| Gln | Thr | Ile | Ser | Thr | Trp | Leu | Ala | Trp | Tyr | Gln | Gln | Thr | Pro | Arg | Lys | |
| | | | 50 | | | | 55 | | | | | 60 | | | | |
| GCC | CCT | AAA | CTC | ATG | ATC | TAT | AAG | GCG | TCT | ATT | TTA | GAA | AAT | GGG | GTC | 240 |
| Ala | Pro | Lys | Leu | Met | Ile | Tyr | Lys | Ala | Ser | Ile | Leu | Glu | Asn | Gly | Val | |
| 65 | | | | 70 | | | | | 75 | | | | | | 80 | |
| CCA | TCA | AGG | TTC | AGC | GGC | AGT | GGA | TCT | GGG | ACA | GAA | TTC | ACT | CTC | ACC | 288 |
| Pro | Ser | Arg | Phe | Ser | Gly | Ser | Gly | Ser | Gly | Thr | Glu | Phe | Thr | Leu | Thr | |
| | | | | 85 | | | | | 90 | | | | | 95 | | |
| ATC | AGC | AGC | CTG | CAG | CCT | GAA | GAT | TTT | GCA | ACT | TAT | TAC | TGT | CAA | CAG | 336 |
| Ile | Ser | Ser | Leu | Gln | Pro | Glu | Asp | Phe | Ala | Thr | Tyr | Tyr | Cys | Gln | Gln | |
| | | | 100 | | | | | 105 | | | | | 110 | | | |
| TAT | AAG | AGT | TAT | CCC | TGG | ACG | TTC | GGC | CAA | GGG | ACC | AAG | GTG | GAA | ATC | 384 |
| Tyr | Lys | Ser | Tyr | Pro | Trp | Thr | Phe | Gly | Gln | Gly | Thr | Lys | Val | Glu | Ile | |
| | | 115 | | | | | 120 | | | | | 125 | | | | |
| AAA | | | | | | | | | | | | | | | | 387 |
| Lys | | | | | | | | | | | | | | | | |

( 2 ) INFORMATION FOR SEQ ID NO:2:

( i ) SEQUENCE CHARACTERISTICS:
        ( A ) LENGTH: 129 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

| | | | | | | | | | | | | | | | |
|---|---|---|---|---|---|---|---|---|---|---|---|---|---|---|---|
| Met | Asp | Met | Arg | Val | Pro | Ala | Gln | Leu | Leu | Gly | Leu | Leu | Leu | Leu | Trp |
| 1 | | | | 5 | | | | | 10 | | | | | 15 | |
| Leu | Pro | Gly | Ala | Lys | Cys | Asp | Ile | Gln | Met | Thr | Gln | Ser | Pro | Ser | Thr |
| | | | 20 | | | | | 25 | | | | | 30 | | |
| Leu | Ser | Ala | Ser | Val | Gly | Asp | Arg | Val | Thr | Ile | Thr | Cys | Arg | Ala | Ser |
| | | | 35 | | | | 40 | | | | | 45 | | | |
| Gln | Thr | Ile | Ser | Thr | Trp | Leu | Ala | Trp | Tyr | Gln | Gln | Thr | Pro | Arg | Lys |
| | | | 50 | | | | 55 | | | | | 60 | | | |
| Ala | Pro | Lys | Leu | Met | Ile | Tyr | Lys | Ala | Ser | Ile | Leu | Glu | Asn | Gly | Val |
| 65 | | | | 70 | | | | | 75 | | | | | | 80 |
| Pro | Ser | Arg | Phe | Ser | Gly | Ser | Gly | Ser | Gly | Thr | Glu | Phe | Thr | Leu | Thr |
| | | | | 85 | | | | | 90 | | | | | 95 | |
| Ile | Ser | Ser | Leu | Gln | Pro | Glu | Asp | Phe | Ala | Thr | Tyr | Tyr | Cys | Gln | Gln |
| | | | 100 | | | | | 105 | | | | | 110 | | |
| Tyr | Lys | Ser | Tyr | Pro | Trp | Thr | Phe | Gly | Gln | Gly | Thr | Lys | Val | Glu | Ile |
| | | 115 | | | | | 120 | | | | | 125 | | | |
| Lys | | | | | | | | | | | | | | | |

( 2 ) INFORMATION FOR SEQ ID NO:3:

( i ) SEQUENCE CHARACTERISTICS:
        ( A ) LENGTH: 441 base pairs ( B ) TYPE: nucleic acid
( C ) STRANDEDNESS: single
( D ) TOPOLOGY: linear ( i i ) MOLECULE TYPE: cDNA ( i i i ) HYPOTHETICAL: NO ( i v ) ANTI-SENSE: NO ( i x ) FEATURE:
  ( A ) NAME/KEY: CDS
  ( B ) LOCATION: 1..441

( x i ) SEQUENCE DESCRIPTION: SEQ ID NO:3:

| ATG | GAC | TGG | ACC | TGG | AGG | TTC | CTC | TTT | GTG | GTG | GCA | GCA | GCT | ACA | GGT | 48 |
| Met | Asp | Trp | Thr | Trp | Arg | Phe | Leu | Phe | Val | Val | Ala | Ala | Ala | Thr | Gly | |
| 1 | | | | 5 | | | | | 10 | | | | | 15 | | |

| GTC | CTG | TCC | CAG | GTG | CAG | TTG | GTG | CAG | TCT | GGG | GCT | GAG | GTG | AAG | AAG | 96 |
| Val | Leu | Ser | Gln | Val | Gln | Leu | Val | Gln | Ser | Gly | Ala | Glu | Val | Lys | Lys | |
| | | | 20 | | | | | 25 | | | | | 30 | | | |

| CCT | GGG | TCC | TCG | GTG | AAG | GTC | TCC | TGC | AAG | GCT | TCT | GGA | GGC | ACC | TTC | 144 |
| Pro | Gly | Ser | Ser | Val | Lys | Val | Ser | Cys | Lys | Ala | Ser | Gly | Gly | Thr | Phe | |
| | | | 35 | | | | | 40 | | | | | 45 | | | |

| AGC | AAC | TTT | GCT | ATC | AGC | TGG | GTG | CGA | CAG | GCC | CCT | GGA | CAA | GGG | CTT | 192 |
| Ser | Asn | Phe | Ala | Ile | Ser | Trp | Val | Arg | Gln | Ala | Pro | Gly | Gln | Gly | Leu | |
| | 50 | | | | | 55 | | | | | 60 | | | | | |

| GAG | TGG | ATG | GGG | CGC | ATC | ATG | CCT | CTC | TTT | GTT | ACG | TCC | ACC | TAC | GCA | 240 |
| Glu | Trp | Met | Gly | Arg | Ile | Met | Pro | Leu | Phe | Val | Thr | Ser | Thr | Tyr | Ala | |
| 65 | | | | | 70 | | | | | 75 | | | | | 80 | |

| CAG | AAG | TTC | CAG | GGC | AGA | GTC | ACG | ATT | AGC | GCG | GAC | GCC | TCT | ACG | AGC | 288 |
| Gln | Lys | Phe | Gln | Gly | Arg | Val | Thr | Ile | Ser | Ala | Asp | Ala | Ser | Thr | Ser | |
| | | | | 85 | | | | | 90 | | | | | 95 | | |

| ACA | GCC | TAC | ATG | GAG | CTG | AGC | AGC | CTG | AGA | TCT | GAC | GAC | ACG | GCC | ATG | 336 |
| Thr | Ala | Tyr | Met | Glu | Leu | Ser | Ser | Leu | Arg | Ser | Asp | Asp | Thr | Ala | Met | |
| | | | 100 | | | | | 105 | | | | | 110 | | | |

| TAT | TAC | TGT | GCG | AGA | GAC | ATA | ACA | GCA | CCT | GGA | GCC | GCA | CCC | ACC | CCC | 384 |
| Tyr | Tyr | Cys | Ala | Arg | Asp | Ile | Thr | Ala | Pro | Gly | Ala | Ala | Pro | Thr | Pro | |
| | | 115 | | | | | 120 | | | | | 125 | | | | |

| CTG | AAT | TTC | TAC | GGC | ATG | GAC | GTC | TGG | GGC | CAA | GGG | ACC | ACG | GTC | ACC | 432 |
| Leu | Asn | Phe | Tyr | Gly | Met | Asp | Val | Trp | Gly | Gln | Gly | Thr | Thr | Val | Thr | |
| | 130 | | | | | 135 | | | | | 140 | | | | | |

| GTC | TCC | TCA | | | | | | | | | | | | | | 441 |
| Val | Ser | Ser | | | | | | | | | | | | | | |
| 145 | | | | | | | | | | | | | | | | |

( 2 ) INFORMATION FOR SEQ ID NO:4:

( i ) SEQUENCE CHARACTERISTICS:
  ( A ) LENGTH: 147 amino acids
  ( B ) TYPE: amino acid
  ( D ) TOPOLOGY: linear ( i i ) MOLECULE TYPE: protein ( x i ) SEQUENCE DESCRIPTION: SEQ ID NO:4:

| Met | Asp | Trp | Thr | Trp | Arg | Phe | Leu | Phe | Val | Val | Ala | Ala | Ala | Thr | Gly |
| 1 | | | | 5 | | | | | 10 | | | | | 15 | |

| Val | Leu | Ser | Gln | Val | Gln | Leu | Val | Gln | Ser | Gly | Ala | Glu | Val | Lys | Lys |
| | | | 20 | | | | | 25 | | | | | 30 | | |

| Pro | Gly | Ser | Ser | Val | Lys | Val | Ser | Cys | Lys | Ala | Ser | Gly | Gly | Thr | Phe |
| | | | 35 | | | | | 40 | | | | | 45 | | |

| Ser | Asn | Phe | Ala | Ile | Ser | Trp | Val | Arg | Gln | Ala | Pro | Gly | Gln | Gly | Leu |
| | 50 | | | | | 55 | | | | | 60 | | | | |

```
Glu  Trp  Met  Gly  Arg  Ile  Met  Pro  Leu  Phe  Val  Thr  Ser  Thr  Tyr  Ala
 65                        70                      75                        80

Gln  Lys  Phe  Gln  Gly  Arg  Val  Thr  Ile  Ser  Ala  Asp  Ala  Ser  Thr  Ser
                     85                      90                        95

Thr  Ala  Tyr  Met  Glu  Leu  Ser  Ser  Leu  Arg  Ser  Asp  Asp  Thr  Ala  Met
               100                      105                      110

Tyr  Tyr  Cys  Ala  Arg  Asp  Ile  Thr  Ala  Pro  Gly  Ala  Ala  Pro  Thr  Pro
          115                      120                      125

Leu  Asn  Phe  Tyr  Gly  Met  Asp  Val  Trp  Gly  Gln  Gly  Thr  Thr  Val  Thr
          130                     135                       140

Val  Ser  Ser
145
```

HUMAN ANTIBODIES AGAINST VARICELLA-ZOSTER VIRUS

CROSS-REFERENCE TO RELATED APPLICATION

This application is a continuation-in-part of U.S. Ser. No. 08/098,479, filed Jul. 28, 1993, now abandoned.

TECHNICAL FIELD

The invention relates generally to the production and use of human monoclonal antibodies against Varicella-zoster virus.

BACKGROUND

Varicella-zoster virus (VZV) is one of the six well-known viruses of the human herpesvirus family, together with herpes simplex virus types I and II, cytomegalovirus, Epstein-Barr virus and human herpesvirus 6. VZV causes chickenpox and herpes zoster. Chickenpox is a normally benign disease that is acquired by most children in developed countries and is characterized by mild systemic effects and the characteristic varicella skin rash. However, it can have significant morbidity and even mortality in neonates and in immunocompromised patients, especially leukemic children. In such patients, complications include widespread visceral dissemination of the virus, varicella pneumonia, and encephalitis. For unknown reasons, chickenpox in adults is often more severe than in children and more likely to have complications. Infection with chickenpox almost always provides life-long immunity to subsequent re-infection.

Herpes zoster, also called shingles, is caused by the reactivation of VZV that has established a latent state in neuronal cells of a ganglion, normally after chickenpox. There are several hundred thousand cases of herpes zoster in the United States annually (Ragozzino et al. (1982), *Medicine* 61:310–316). About 10–20% of adults will have at least one attack of herpes zoster during their lifetime. Reactivation from the latent state appears to be associated with age-associated weakening of the immune system, as the incidence of herpes zoster increases greatly with age and/or treatment with immunosuppressive drugs. In herpes zoster, the reactivated virus travels down the associated sensory nerve from the ganglion to cause the characteristic varicella lesions in the area of skin (dermatome) innervated by that ganglion, while also causing inflammation of the nerve. The areas supplied by the trigeminal nerve and thoracic ganglia T3 - L2 are most often affected, and about 10–15% of cases have ophthalmic involvement. Zoster is often painful, and the lesions require 2–3 weeks to resolve. Like chickenpox, herpes zoster can become disseminated and have severe complications in immunocompromised patients.

Complications from herpes zoster also frequently occur in immunocompetent patients. At least 10% of such patients develop post-herpetic neuralgia pain continuing after healing of the lesions. The incidence of post-herpetic neuralgia increases sharply with age of the patient, as does the probability that it will last longer than a month. Moreover, as the population ages in developed countries, both the absolute incidence of herpes zoster and of post-herpetic neuralgia can be expected to increase. The neuralgia resolves within 2 months in about 50% of the affected patients and within 1 year in 70–80%, but can last longer in a fraction of patients and can be severe and disabling. The cause of post-herpetic neuralgia is unknown.

Presently available treatments and protective measures against VZV are not entirely satisfactory. A live attenuated vaccine for VZV provides some protection (Takahashi (1986), *Pediatrics* 78:736–741), but has not yet been approved in the United States. High dose acyclovir speeds recovery from chickenpox, although it is not generally required or recommended in normal children because of possible side-effects. Acyclovir also halts progression and speeds resolution of herpes zoster, but is not known to have any effect on post-herpetic neuralgia. Vidarabine is effective against VZV, but is even more toxic than acyclovir. VZIG, pooled human immunoglobulin with a high titer to VZV, is partially effective in preventing or attenuating subsequent varicella infection when given prophylactically, but it has no effect on established disease (Gershon et al. (1974), *N. Eng. J. Med.* 290:243–245). Moreover, pooled human collections of polyclonal antibody may also show poor reproducibility of results and create a risk of pathogenic contamination.

The limited effectiveness of human polyclonal sera has led some investigators to attempt to produce human monoclonal antibodies against VZV. Human monoclonals antibodies are advantageous compared with those from mouse or other species, because, inter alia, they exhibit little or no immunogenicity in a human host. However, techniques for producing human antibodies have met with only limited success. For example, immortalization of immunized human lymphocytes with Epstein-Barr virus, while successful in forming monoclonal-antibody secreting cultures, has often failed to produce cells having sufficiently long lifespans to provide a reliable source of the desired antibody. Kozbor et al. (1982), *Hybridoma* 1:323. In another approach, hybridomas generated by fusion of immunized human lymphoid cell lines with mouse myelomas, have been found to exhibit chromosomal instability. Nowinski et al. (1980), *Science* 210:537; Lane et al. (1982), *J. Exp. Med.* 155:133 (1982). Another approach has been described by Ostberg et al. (1983), *Hybridoma* 2:361–367 and Engelman et al., U.S. Pat. No. 4,634,666. This method entails fusing a mouse myeloma cell with a nonimmunized human B-lymphocyte to form a xenogenic fusion cell. The fusion cell is then fused with an immunized human B-lymphocyte to produce a trioma cell.

With the particular difficulties of producing a human monoclonal antibody compounded by the inherent unpredictability of identifying a first antibody having desirable characteristics against a specific antigen, it is unsurprising that human antibodies produced against VZV to-date have not been shown to possess ideal properties for clinical use. Engelman et al., supra, discuss isolation of two human anti-VZV monoclonal antibodies that exhibit only a low degree of neutralizing activity against the virus ($IC_{50}$ of approximately 5 µg/ml). Foung et al. (1985), *J. Infec. Diseases* 152:280 discuss isolation of two human antibodies to undesignated VZV antigens that also exhibit a low degree of neutralizing activity against the virus ($IC_{50}$ of 1 to 5 µg/ml). The complement-dependence and epitope specificity of these antibodies is not reported. Masuho et al., U.S. Pat. No. 4,950,595 discuss isolation of three human monoclonal antibodies against VZV virus. These antibodies exhibited complement-dependent neutralizing activities having $IC_{50}$'s ranging from 0.13–6.6 µg/ml. The antibody with the strongest neutralizing activity was reported to bind to the VZV glycoprotein I antigen. Further examples of human monoclonal antibodies against VZV are discussed by Sasaki et al., EP 481089. Although a human monoclonal antibody against the gpIII subunit allegedly showed some potentially useful characteristics, Sasaki et al. report that antibodies against the VZV glycoprotein I and II subunits exhibited only weak neutralizing activity.

Based on the foregoing, it is apparent that a need exists for human monoclonal antibodies exhibiting strong neutralizing activity, particularly complement-independent neutralizing activity, against certain VZV antigens, especially the glycoprotein II (gpII) antigen. The present invention fulfills this and other needs.

SUMMARY OF THE INVENTION

In one embodiment of the invention, human monoclonal antibodies against Varicella-zoster virus (VZV) are provided. The antigen-specificity of these human monoclonal antibodies is defined by their capacity to compete with a specific monoclonal antibody, designated 93KA9, for binding to VZV. Binding fragments of these human monoclonal antibodies are also provided. Preferably, the human monoclonal antibodies of the invention exhibit neutralizing activity against VZV, preferably the neutralizing activity is complement-independent, more preferably with $IC_{50}<1$ µg/ml in a cytopathic effect assay, and most preferably with $IC_{50}<0.1$ µg/ml. Preferably, the human monoclonal antibodies also exhibit antibody-dependent cellular cytotoxicity against cells infected with the virus. Preferably, the human monoclonal antibodies exhibit neutralizing activity against at least two strains of VZV.

In another aspect of the invention, cell lines producing human monoclonal antibodies against VZV are provided. Some of these cell lines are trioma cell lines formed by fusion of three cells. Initially, a xenogenic hybrid cell is formed by fusing a mouse myeloma cell with a human peripheral B lymphocyte. The hybrid cell is in turn fused with a B lymphoid cell derived from a human donor exposed to an antigen of VZV. Frequently, the human donor has been exposed to a natural infection of the virus. Also provided are cell lines comprising recombinant DNA segments encoding the heavy and light chains of the human monoclonal antibodies described above. The DNA segments are operably linked to promoters and thereby rendered capable of being expressed in the cell lines.

Also provided are recombinant DNA molecules comprising DNA segments encoding the heavy or light chains of the human monoclonal antibodies described above. The DNA segments encode at least one CDR region of either the heavy or light chain of such an antibody. Usually, the DNA segments encode the light or heavy chain variable region, or the entire light or heavy chain.

Also provided are pharmaceutical compositions comprising the human monoclonal antibodies or their binding fragments described above, and methods of diagnosis and treatment using the same.

BRIEF DESCRIPTION OF THE DRAWINGS

FIG. 4: Sequences of the 93KA9 antibody light chain (FIG. 4A) (SEQ. ID NO. 1) and heavy chain (FIG. 4B) (SEQ. ID NO. 3) variable region cDNAs and the translated amino acid sequences (1-letter code) (SEQ. ID NOS. 2 and 4, respectively. The first amino acid of the mature light chain and of the mature heavy chain is double underlined, and the three complementarity determining regions (CDRs) in each chain are underlined.

DEFINITIONS

Figure 1:
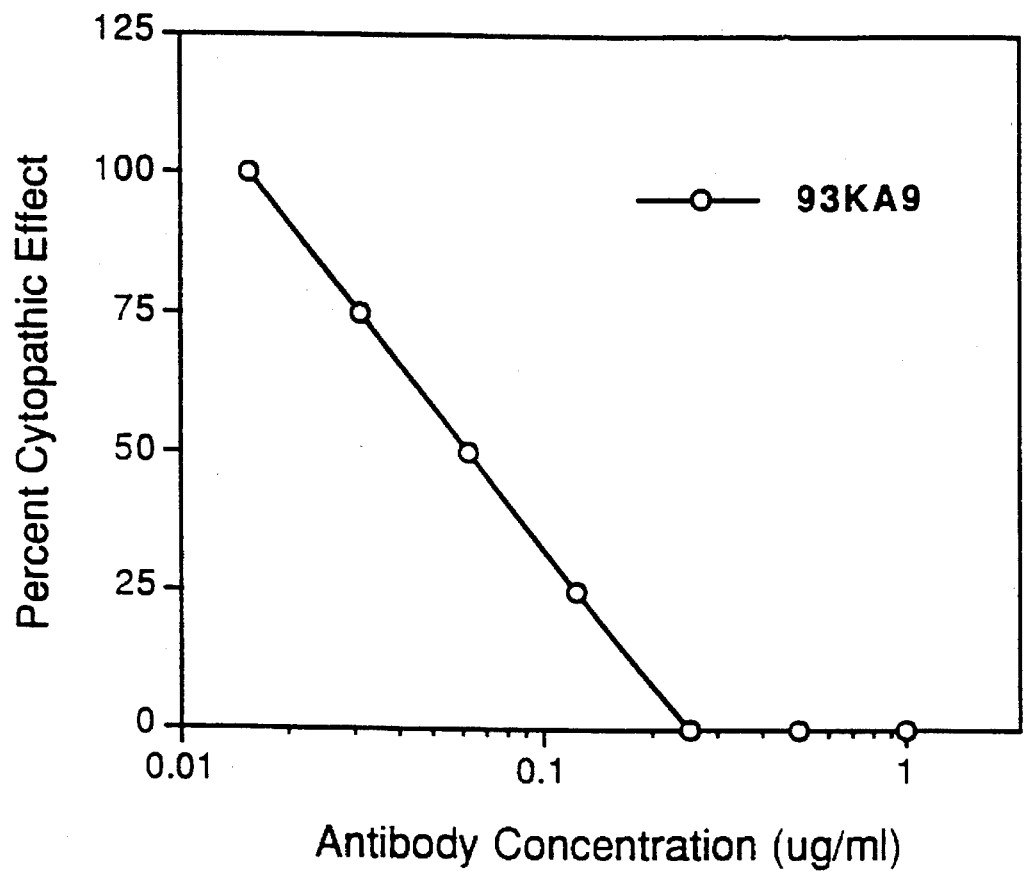
FIG. 1: Neutralization of VZV by 93KA9 antibody. The percentage cytopathic effect was estimated by microscopic visual examination of the infected cells (100%=total cell layer destruction, 0%=no visible cytopathic effect).

As applied to polypeptides, the term "substantial identity" means that two peptide sequences, when optimally aligned, such as by the programs BLAZE (Intelligenetics) GAP or BESTFIT using default gap weights, share at least 70 percent or 85 percent sequence identity, preferably at least 90 percent sequence identity, more preferably at least 95 percent sequence identity or more (e.g., 99 percent sequence identity). Preferably, residue positions which are not identical differ by conservative amino acid substitutions.

Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acids substitution groups are: valine-leucine-isoleucine, phenylalanine-tyrosine, lysine-arginine, alanine-valine, and asparagine-glutamine.

The term "substantially pure" means an object species is the predominant species present (i.e., on a molar basis it is more abundant than any other individual species in the composition), and preferably a substantially purified fraction is a composition wherein the object species comprises at least about 50 percent (on a molar basis) of all macromolecular species present. Generally, a substantially pure composition will comprise more than about 80 to 90 percent of all macromolecular species present in the composition. Most preferably, the object species is purified to essential homogeneity (contaminant species cannot be detected in the composition by conventional detection methods) wherein the composition consists essentially of a single macromolecular species.

DETAILED DESCRIPTION

I. Human Antibodies Against VZV Virus

According to one embodiment of the invention, human monoclonal antibodies against VZV virus in substantially purified form are provided.

1. VZV virus

Like other herpes viruses, VZV has a large, double-stranded DNA core within an icosahedral capsid of protein and is surrounded by an envelope deriving from and of similar composition to the cell membrane (see generally, *Virology,* (B. N. Fields, ed., Raven Press, 1990), pp. 2011–2054. Several different strains of VZV are known including K.McC, Ellen, Caqu, Batson, Kawaguichi, Oka, Kobayashi and Tubo. The VZV envelope contains numerous protrusions, or "spikes" which consist of glycoproteins. The VZV envelope contains at least five distinct glycoproteins, designated gpI, gpII, gpIII, gpIV and gpV, most of which occur in various molecular weight forms. The functions of these glycoproteins are not completely known, but several may be involved in adsorption to, and penetration of, cells. GpII is of particular importance as an antigenic determinant in the present invention. It is believed that gpII, which is the homolog of the gB glycoprotein of HSV, is important for the initial adsorption phase of cell infection.

VZV may be grown in a variety of human and other cell lines. The virus is always cytolytic in vitro, although it has the capacity to infect cells latently in vivo, like the other herpes viruses. VZV is very labile and temperature sensitive. Infected cell cultures release little if any free virus, with the virus instead remaining cell-associated. Free virus can be released by sonication, but yield is usually poor, and the cell-free virus adsorbs slowly and inefficiently to tissue culture cells. Hence, the virus is usually propagated in vitro using infected cells. After infection of the new cells, a cytopathic effect can be seen within 24 hr and reaches 80–90% in 2–3 days.

2. General Characteristics of Antibodies

Antibodies or immunoglobulins are typically composed of four covalently bound peptide chains. For example, an IgG antibody has two light chains and two heavy chains. Each light chain is covalently bound to a heavy chain. In turn each heavy chain is covalently linked to the other to form a "Y" configuration, also known as an immunoglobulin conformation. Fragments of these molecules, or even heavy or light chains alone, may bind antigen. Antibodies, fragments of antibodies, and individual chains are also referred to herein as immunoglobulins.

A normal antibody heavy or light chain has an N-terminal ($NH_2$) variable (V) region, and a C-terminal (—COOH) constant (C) region. The heavy chain variable region is referred to as $V_H$ (including, for example, $V_\gamma$), and the light chain variable region is referred to as $V_L$ (including $V_\kappa$ or $V_\lambda$). The variable region is the part of the molecule that binds to the antibody's cognate antigen, while the Fc region (the second and third domains of the C region) determines the antibody's effector function (e.g., complement fixation, opsonization). Full-length immunoglobulin or antibody "light chains" (generally about 25 Kd, about 214 amino acids) are encoded by a variable region gene at the N-terminus (generally about 110 amino acids) and a κ (kappa) or λ (lambda) constant region gene at the COOH-terminus-Full-length immunoglobulin or antibody "heavy chains" (generally about 50 Kd, about 446 amino acids), are similarly encoded by a variable region gene (generally encoding about 116 amino acids) and one of the constant region genes, e.g., gamma (encoding about 330 amino acids). Typically, the "$V_L$" will include the portion of the light chain encoded by the $V_L$ and/or $J_L$ (J or joining region) gene segments and the "$V_H$" will include the portion of the heavy chain encoded by the $V_H$, and/or $D_H$ (D or diversity region) and $J_H$ gene segments. See generally, Roitt et al., *Immunology,* Chapter 6 (2d ed. 1989) and Paul, *Fundamental Immunology;* Raven Press (2d ed. 1989).

An immunoglobulin light or heavy chain variable region consists of a "framework" region interrupted by three hypervariable regions, also called complementarity-determining regions or CDRs. The extent of the framework region and CDRs have been defined (see Kabat et al. (1987), "Sequences of Proteins of Immunological Interest," U.S. Department of Health and Human Services; Chothia et al. (1987), *J. Mol. Biol.* 196:901–917. The sequences of the framework regions of different light or heavy chains are relatively conserved within a species. The framework region of an antibody, that is the combined framework regions of the constituent light and heavy chains, serves to position and align the CDRs in three dimensional space. The CDRs are primarily responsible for binding to an epitope of an antigen. The CDRs are typically referred to as CDR1, CDR2, and CDR3, numbered sequentially starting from the N-terminus.

The two types of light chains, κ and λ, are referred to as isotypes. Isotypic determinants typically reside in the constant region of the light chain, also referred to as the $C_L$ in general, and $C_\kappa$ or $C_\lambda$ in particular. Likewise, the constant region of the heavy chain molecule, also known as $C_H$, determines the isotype of the antibody. Antibodies are referred to as IgM, IgD, IgG, IgA, and IgE depending on the heavy chain isotype. The isotypes are encoded in the mu (μ), delta (Δ), gamma (γ), alpha (α), and epsilon (ε) segments of the heavy chain constant region, respectively. In addition, there are a number of γ subtypes.

The heavy chain isotypes determine different effector functions of the antibody, such as opsonization or complement fixation. In addition, the heavy chain isotype determines the secreted form of the antibody. Secreted IgG, IgD, and IgE isotypes are typically found in single unit or monomeric form. Secreted IgM isotype is found in pentameric form; secreted IgA can be found in both monomeric and dimeric form.

3. Methods of Producing Human Monoclonal Antibodies against VZV

The human antibodies of the present invention are usually produced initially in trioma cells, although other approaches are also possible. (See, e.g., Larrick et al., U.S. Pat. No. 5,001,065, for review). Genes encoding the antibodies are then cloned and expressed in other cells, particularly, non-human mammalian cells.

a. Trioma Technology

The general approach for producing human antibodies by trioma technology has been described by Ostberg et al. (1983), *Hybridoma* 2:361–367, Ostberg, U.S. Pat. No. 4,634,664, and Engelman et al., U.S. Pat. No. 4,634,666. The antibody-producing cell lines obtained by this method are called triomas, because they are descended from three cells—two human and one mouse. Triomas have been found to produce antibody more stably than ordinary hybridomas made from human cells.

Preparation of trioma cells requires an initial fusion of a mouse myeloma cell line with unimmunized human peripheral B lymphocytes. This fusion generates a xenogenic hybrid cell containing both human and mouse chromosomes. See Engelman, supra. Xenogenic cells that have lost the capacity to secrete antibodies are selected. Preferably, a xeonogenic cell is selected that is resistant to 8-azaguanine. Cells possessing resistance to 8-azaguanine are unable to propagate on hypoxanthine-aminopterin-thymidine (HAT) or azaserine-hypoxanthine (AH) media.

The capacity to secrete antibodies is conferred by a further fusion between the xenogenic cell and B-lymphocytes immunized against VZV or an antigen thereof. The B-lymphocytes are obtained from the spleen, blood or lymph nodes of human donor. The B-lymphocytes are usually obtained from an individual who has been naturally infected with VZV virus. However, B-lymphocytes can also be obtained from an individual who has been immunized with an attenuated viral vaccine, a viral protein or a peptide fragment of a viral protein. If antibodies against a specific antigen or epitope are desired, it is preferable to use that antigen or epitope thereof as the immunogen rather than whole virus. Alternatively, B-lymphocytes are obtained from an unimmunized individual and stimulated with VZV virus, or an antigen thereof, in vitro. In a further variation, B-lymphocytes are obtained from an infected, or otherwise immunized individual, and then hyperimmunized by exposure to virus or viral antigen for about seven to fourteen days, in vitro.

The immunized B-lymphocytes prepared by one of the above procedures are fused with a xeonogenic hybrid cell by well known methods. For example, the cells are treated with 40–50% polyethylene glycol of MW 1000–4000, at about 37 degrees, for about 5–10 min. Cells are separated from the fusion mixture and propagated in media selective for the desired hybrids. When the xenogenic hybrid cell is resistant to 8-azaguanine, immortalized trioma cells are conveniently selected by successive passage of cells on HAT or AH medium. Other selective procedures are, of course, possible depending on the nature of the cells used in fusion. Clones secreting antibodies having the required binding specificity are identified by assaying the trioma culture medium for the ability to bind to VZV or an antigen thereof. Triomas producing human antibodies having the desired specificity are subcloned by the limiting dilution technique and grown in vitro in culture medium, or are injected into selected host animals and grown in vivo. The trioma cell lines obtained are then tested for the ability to bind VZV, or a polypeptide thereof. Antibodies are separated from the resulting culture medium or body fluids by conventional antibody-fractionation procedures, such as ammonium sulfate precipitation, DEAE cellulose chromatography and affinity chromatography.

b. Recombinant DNA technology

Although triomas are genetically stable they do not produce antibodies at very high levels. Expression levels can be increased by cloning antibody genes from the trioma into one or more expression vectors, and transforming the vector into a cell line such as the cell lines typically used for expression of recombinant or humanized immunoglobulins. As well as increasing yield of antibody, this strategy offers the additional advantage that immunoglobulins are obtained from a cell line that does not have a human component, and does not therefore need to be subjected to the especially extensive viral screening required for human cell lines.

The genes encoding the heavy and light chains of immunoglobulins secreted by trioma cell lines are cloned according to methods, including the polymerase chain reaction, known in the art, and described in Sambrook et al., Molecular *Cloning: A Laboratory Manual*, (2nd ed., Cold Spring Harbor, N.Y., 1989; Berger & Kimmel, *Methods in Enzymology, Volume* 152, *Guide to Molecular Cloning Techniques*, (Academic Press, Inc., San Diego, Calif., 1987); Co et al. (1992), *J. Immunol.*, 148:1149. For example, genes encoding heavy and light chains are cloned from a trioma's genomic DNA or cDNA produced by reverse transcription of the trioma's RNA. Cloning is accomplished by conventional techniques including the use of PCR primers that hybridize to the sequences flanking or overlapping the genes, or segments of genes, to be cloned.

Typically, recombinant constructs comprise DNA segments encoding a complete human immunoglobulin heavy chain and/or a complete human immunoglobulin light chain of an immunoglobulin expressed by a trioma cell line. Alternatively, DNA segments encoding only a portion of the primary antibody genes are produced, which portions possess binding and/or effector activities. Other recombinant constructs contain segments of trioma cell line immunoglobulin genes fused to segments of other immunoglobulin genes, particularly segments of other human constant region sequences (heavy and/or light chain). Human constant region sequences can be selected from various reference sources, including but not limited to those listed in Kabat et al., supra.

In addition to the DNA segments encoding VZV immunoglobulins or fractions thereof, other substantially homologous modified immunoglobulins can be readily designed and manufactured utilizing various recombinant DNA techniques known to those skilled in the art such as site-directed mutagenesis (see Gillman & Smith (1979), *Gene*, 8:81–97; Roberts et al. (1987), *Nature*, 328:731–734). Such modified segments will usually retain antigen binding capacity and/or effector function. Moreover, the modified segments are usually not so far changed from the original trioma genomic sequences to prevent hybridization to these sequences under stringent conditions. Because, like many genes, immunoglobulin genes contain separate functional regions, each having one or more distinct biological activities, the genes may be fused to functional regions from other genes to produce fusion proteins (e.g., immunotoxins) having novel properties or novel combinations of properties.

The recombinant polynucleotide constructs will typically include an expression control sequence operably linked to the coding sequences, including naturally-associated or heterologous promoter regions. Preferably, the expression control sequences will be eukaryotic promoter systems in vectors capable of transforming or transfecting eukaryotic host cells. Once the vector has been incorporated into the appropriate host, the host is maintained under conditions suitable for high level expression of the nucleotide sequences, and the collection and purification of the human anti-VZV immunoglobulins.

These expression vectors are typically replicable in the host organisms either as episomes or as an integral part of the host chromosomal DNA. Commonly, expression vectors will contain selection markers, e.g., ampicillin-resistance or hygromycin-resistance, to permit detection of those cells transformed with the desired DNA sequences.

In general, prokaryotes can be used for cloning the DNA sequences encoding a human anti-CMV immunoglobulin chain. *E. coli* is one prokaryotic host particularly useful for cloning the DNA sequences of the present invention. Microbes, such as yeast are also useful for expression. Saccharomyces is a preferred yeast host, with suitable vectors having expression control sequences, an origin of replication, termination sequences and the like as desired. Typical promoters include 3-phosphoglycerate kinase and other glycolytic enzymes. Inducible yeast promoters include, among others, promoters from alcohol dehydrogenase 2, isocytochrome C, and enzymes responsible for maltose and galactose utilization.

Mammalian cells are a particularly preferred host for expressing nucleotide segments encoding immunoglobulins or fragments thereof. (See Winnacker, *From Genes to Clones*, (VCH Publishers, N.Y., 1987). A number of suitable host cell lines capable of secreting intact heterologous proteins have been developed in the art, and include CHO cell lines, various COS cell lines, HeLa cells, L cells and myeloma cell lines. Preferably, the cells are nonhuman. Expression vectors for these cells can include expression control sequences, such as an origin of replication, a promoter, an enhancer (Queen et al. (1986), *Immunol. Rev.* 89:49), and necessary processing information sites, such as ribosome binding sites, RNA splice sites, polyadenylation sites, and transcriptional terminator sequences. Preferred expression control sequences are promoters derived from endogenous genes, cytomegalovirus, SV40, adenovirus, bovine papillomavirus, and the like. See Co et al. (1992), *J. Immunol.* 148:1149.

The vectors containing the DNA segments of interest can be transferred into the host cell by well-known methods, depending on the type of cellular host. For example, calcium chloride transfection is commonly utilized for prokaryotic cells, whereas calcium phosphate treatment, electroporation, lipofection, biolistics or viral-based transfection may be used for other cellular hosts. Other methods used to transform mammalian cells include the use of polybrene, protoplast fusion, liposomes, electroporation, and microinjection (see, generally, Sambrook et al., supra).

Once expressed, human anti-VZV immunoglobulins of the invention can be purified according to standard procedures of the art, including HPLC purification, fraction column chromatography, gel electrophoresis and the like (see, generally, Scopes, *Protein Purification,* (Springer-Verlag, NY, 1982 ) ).

4. Human monoclonal antibodies against VZV

Irrespective of their method of preparation, the human monoclonal antibodies of the present invention exhibit specific binding to VZV. Specific binding exists when the dissociation constant for antibody binding to the virus or an antigen thereof is $\leq 1$ μM, preferably $\leq 100$ nM and most preferably $\leq 1$ nM. Preferably, the antibody binds to a gpII determinant of VZV. The ability of an antibody to bind to gpII can be detected by labelling the antibody of interest directly, or the antibody may be unlabelled and binding detected indirectly using various sandwich assay formats. See, e.g., Harlow & Lane, *Antibodies: A Laboratory Manual* (Cold Spring Harbor Publications, NY, 1988). Antibodies having this binding specificity are more likely to share the advantageous properties exhibited by the 93KA9, discussed infra. A cell line producing the antibody 93KA9, designated TC93KA9 or PDL93KA9, was deposited on Feb. 8, 1994, with American Type Culture Collection 12301 Parklawn Drive, Rockville, Md. 20852-1776 under the Budapest Treaty and received the ATCC designation HB 11549.

Preferably, the antibodies of the invention block or compete with binding of the 93KA9 antibody to VZV virus or the gpII antigen thereof. The capacity to block, or compete with, 93KA9 binding indicates that an antibody binds to the same or similar epitope as that defined by 93KA9, or to an epitope which is sufficiently proximal to the epitope bound by 93KA9 to inhibit binding of 93KA9 to VZV. Such antibodies are especially likely to share the advantageous properties identified for 93KA9. The capacity to block or compete with 93KA9 may be determined by a variety of methods. For example, supernatants of antibody-secreting cells are screened with labelled 93KA9 antibody in a competition assay of which numerous types are known (see, e.g., U.S. Pat. Nos. 3,376,110, and 4,016,043, and Harlow & Lane, supra). A test substance competes with a reference for specific binding to an antigen when an excess of the test substance substantially inhibits binding of the reference in a competition assay. Substantially inhibits means that the test substance reduces specific binding of the reference usually by at least 10%, 25%, 50%, 75%, or 90%.

The human monoclonal antibodies of the present invention preferably exhibit neutralizing activity against VZV so as to be of value in prophylactic and/or therapeutic treatment of the virus. The presence of neutralizing activity is shown by the ability of an antibody when mixed with the virus in vitro, to lower the titer of infectious virus. See Example 3 and Grose et al. (1979), *J. Infectious Disease* 139:142. Neutralizing activity is quantified by measurement of $IC_{50}$, the concentration of antibody in μg/ml required to reduce the titer of virus by 50%, especially as measured by reduction of cytopathic effect (CPE). The lower the value of $IC_{50}$, the stronger the neutralizing activity exhibited by the antibody, and the greater its potential as a therapeutic agent. Usually, the human immunoglobulins of the invention exhibit an $IC_{50}$ of about 0.001 to 10 μg/ml, more frequently less than 1 μg/ml, and most frequently less than 0.1 μg/ml, e.g., about 0.06 μg/ml. In this context, the term "about" encompasses typical experimental variations that may occur in measurement of $IC_{50}$.

Preferably, the antibodies of the invention exhibit complement-independent neutralizing activity. Such antibodies effectively eliminate virus infectivity merely by binding to the virus. Other antibodies can bind to a virus, but are able to kill the virus, if at all, only via activation of complement. In this mechanism, binding of antibody to cell or viral membrane bound antigens initiates a chain of events leading to complement-mediated lysis of the cell or viral membrane. This requirement for complex interactions with another biological system usually renders complement-dependent antibodies less effective as therapeutic agents than directly neutralizing antibodies. Moreover, complement activation can also cause inflammation of adjacent cells leading to undesirable side effects. These side effects are, of course, avoided by the use of complement-independent neutralizing antibodies. The presence of complement-independent neutralizing activity is determined by performing the neutralization test in the presence and absence of exogenously supplied complement. If the same or similar reduction in titer is observed irrespective of the presence of complement, the neutralizing activity is complement independent.

A further desirable characteristic of human antibodies against VZV is the capacity to induce antibody-dependent cellular cytotoxicity (ADCC) against virally infected cells. Such activity supplements the direct neutralizing activity of the antibodies against the virus, and may play a significant role in clearing viral infection. ADCC is mediated by killer cells having an Fc receptor on their surface, by which they recognize, and exert a cytotoxic activity toward, antibody-coated target cells.

A further desirable characteristic of the antibodies of the present invention is the capacity to recognize and/or neutralize and/or induce ADCC activity against more than one strain of VZV. As discussed in section 1.1, supra, many different variants of VZV are known. However, different members of viral families often possess certain common epitopes. Antibodies directed to such common epitopes are particularly advantageous because they are reactive with multiple strains of the virus. The provision of antibodies reactive against multiple strains of virus allows a single antibody to be used in most therapeutic and diagnostic application. Preferably the monoclonal antibody is reactive with at least two strains of VZV, more preferably at least three, four, five, six, seven, eight, nine or even ten strains of the virus.

Also provided are binding fragments of the human antibodies described above. Fragments of antibodies that retain binding capacity include Fab fragments, F(ab')$_2$ fragments, Fv fragments and unassociated heavy or light chains, and single-chain antibodies.

Many of the immunoglobulins described above can undergo non-critical amino-acid substitutions, additions or deletions in both the variable and constant regions without loss of binding specificity or effector functions, or intolerable reduction of binding affinity (i.e., below about $10^7$ $M^{-1}$). Usually, immunoglobulins incorporating such alterations exhibit substantial sequence identity to a reference immunoglobulin from which they were derived. For example, the mature light chain of antibodies derived from the 93KA9 antibody usually show at least 85% sequence identity to the sequence of the mature light chain of the 93KA9 antibody shown in FIG. 4A. Similarly, the mature heavy chains of 93KA9 derivatives typically show at least 85% sequence identity to the sequence of the mature heavy chain of the 93KA9 antibody shown in FIG. 4B. Occasionally, a mutated immunoglobulin can be selected having the same specificity and increased affinity compared with a reference immunoglobulin from which it was derived. Usually, the affinity of a mutated immunoglobulin is within a factor of 2, 5, 10 or 50 of the reference immunoglobulin. Phage-display technology offers powerful techniques for selecting such immunoglobulins. See, e.g., Dower et al., WO 91/17271; McCafferty et al., WO 92/01047; and Huse, WO 92/06204 (each of which is incorporated by reference in its entirety for all purposes).

II. Cell lines

Also provided are cell lines expressing the antibodies described, supra. The cell line is usually either a trioma cell line expressing endogenous immunoglobulin genes or a nonhuman mammalian cell line expressing exogenous cloned immunoglobulin gene (s) or segments of these gene (s) . In the latter case, the exogenous gene(s) or segment(s) are usually cloned on one or more recombinant DNA segments. The gene(s) or segment(s) are operably linked to one or more promoters to ensure their transcription and translation in the cell. Different genes or segments can be linked to the same or different promoters. The gene(s) or segment(s) can be present on extra chromosomal vectors or can be integrated into the chromosome.

III. Nucleic Acids

Also provided in substantially purified form are DNA segments encoding heavy or light chains of the antibodies described supra. The DNA segments encode at least one CDR regions and usually all three CDR regions from the heavy or light chain of an immunoglobulin. Frequently, a DNA segment encodes all or substantially all of the variable region of a heavy or light chain and is thereby capable of exhibiting antigen binding capacity. Often a nucleic acid encodes an entire heavy or light chain. Because of the degeneracy of the code, a variety of nucleic acid sequences will encode each immunoglobulin amino acid sequence. The desired nucleic acid sequences can be produced by de novo solid-phase DNA synthesis or by PCR mutagenesis of an earlier prepared variant of the desired polynucleotide.

Preferred nucleic acids include those encoding mature light chain variable regions having substantial sequence identity to the mature light chain variable region of the 93KA9 antibody shown in FIG. 4A. Preferred nucleic acids also include those encoding mature heavy chain variable regions having substantial sequence identity to the mature heavy chain variable region of the 93KA9 antibody shown in FIG. 4B.

IV. Methods of Use (a) Diagnostic

The monoclonal antibodies of the present invention are useful for diagnosing infections of VZV by a variety of conventional immunoassay procedures such as ELISA or RIA. In such procedures, the antibody can be labelled directly (e.g., by radioactive or fluorescent label) and immune complexes detected via the label. Usually, however, the antibody is unlabelled and the desired antigen-monoclonal antibody complex is detected with an enzyme-conjugated antibody against the monoclonal antibody. Preferably, the antibody selected for diagnosis will exhibit reactivity with several different strains of VZV, so that diagnosis can be accomplished by a single test. Occasionally, however, it is desirable to distinguish between different strains of VZV virus, in which case, antibodies specific for particular strains of the virus are used.

Kits for carrying out the above described tests will normally contain an antigen immobilizing material, a monoclonal antibody, enzyme-conjugated antibody against the monoclonal antibody and an appropriate substrate. The kits may also contain a suitable buffer for dilution and washing, a post-coating preparation such as bovine serum albumin and directions for carrying out the tests. These components may be packaged and stored in conventional manners.

(b) Antigen purification

Human monoclonal antibodies against VZV glycoprotein II can be used to purify glycoprotein II antigen. The antibodies are immobilized to a solid support and a solution of dispersed proteins is passed over the support. Glycoprotein II binds to the support and is thereby separated from other viral proteins. The purified glycoprotein II, or a fragment thereof, made available by this method can be used as a vaccine. Purified glycoprotein II, and fragments thereof, are also useful for generation and screening of additional monoclonal antibodies exhibiting specific binding to glycoprotein II.

(c) Treatment

In therapeutic applications, a composition comprising a human monoclonal anti-VZV antibody (e.g., 93KA9) is administered to a patient already affected by a VZV-related disease (e.g., chicken pox, shingles) in an amount sufficient to cure, partially arrest, or detectably slow the progression of the condition, and its complications, by neutralizing VZV. An amount adequate to accomplish this is defined as a "therapeutically effective dose" or "efficacious dose." Amounts effective for this use will depend upon the severity of the condition, the general state of the patient, and the route of administration, and combination with other antiviral drugs, if any, but generally range from about 1 mg to about 1 g of human anti-VZV antibody per dose, with single dosage units of from 10 mg to 100 mg per patient being more commonly used. Antibody is usually administered systemically by intravenous infusion. Alternative dosage levels are generally from about 0.25 mg/kg patient bodyweight to approximately 5 mg/kg patient bodyweight, with larger doses occasionally employed. Usually, multiple dosage administrations are performed as a course of therapy.

In prophylactic applications, compositions containing the human monoclonal anti-VZV antibodies or cocktails thereof are administered to a patient not already in a VZV disease state to enhance the patient's resistance or to retard the progression of VZV-related disease. Prophylactic administration is particularly advantageous in immunocompromised patients, such as leukemic children or patients taking immunosuppressive drugs. These patients are particularly susceptible to VZV-mediated diseases and more frequently suffer severe complications from these diseases. The amount of antibody to be administered is a "prophylactically effective dose," the precise amounts of which will depend upon the patient's state of health and general level of immunity, but generally range from 1 mg to 1 g per dose, especially 10 mg to 100 mg per patient.

The pharmaceutical composition used for prophylactic or therapeutic treatment can be in a variety of forms. The preferred form depends on the intended mode of administration and therapeutic application. The compositions may also include, depending on the formulation desired, pharmaceutically-acceptable, non-toxic carriers or diluents, which are defined as vehicles commonly used to formulate pharmaceutical compositions for animal or human administration. The diluent is selected so as not to affect the biological activity of the combination. Examples of such diluents are distilled water, physiological saline, Ringer's solutions, dextrose solution, and Hank's solution. In addition, the pharmaceutical composition or formulation may also include other carriers, adjuvants, or nontoxic, nontherapeutic, nonimmunogenic stabilizers and the like. Typically, a sterile solution of a human monoclonal anti-VZV antibody in an aqueous solvent (e.g., saline) will be administered intravenously.

EXAMPLES

1, Isolation of a human anti-VZV monoclonal antibody

The antibody was prepared using the trioma method of Ostberg et al. (1983), *Hybridoma* 2:361–367. A xenogenic mouse-human cell was produced by fusing the drug resistant mouse cell line SP-2 obtainable, e.g., from the NIGMS Human Genetic Mutant Cell Repository Ref. GM35669A (see U.S. DHHS 1982 Catalog of Cell Lines) with normal human peripheral lymphocytes, by conventional techniques. A large number of hybrids were obtained and, after approximately five weeks, clones were selected which showed fast growth and no antibody production. These cells were selected for resistance to 20 μg/ml of 8-azaguanine. These cells were also sensitive to hypoxanthine-aminopterin-thymidine (HAT) medium indicating their loss of capacity to produce hypoxanthine phosphoribosyl transferase. One of these cell lines was designated SPAZ-4.

Immunized human B cells for fusion with SPAZ-4 were obtained from the spleen of an adult sero-positive for VZV. The isolated splenocytes were stimulated in vitro with a heat-inactivated lysate of VZV-infected cells, and then fused with the mouse-human SPAZ-4 hybridoma cell line. Trioma fusion cells were selected by growth on HAT media. Clonal isolates of HAT resistant cells were separated and screened for production of antibodies against VZV. About 70 triomas producing human antibodies reactive with VZV were isolated. Of these, four cell lines produced antibodies that neutralized VZV in the presence of complement, but only one neutralized VZV efficiently in the absence of complement (see Example 3, for method of determining neutralizing activity). This cell line, designated cell line TC93KA9, produced an antibody, designated 93KA9, which was selected for further characterization. Additional human antibodies with the same antigen specificity and similar or better neutralization ability as 93KA9 can be produced in the same manner by using B cells obtained from additional adults seropositive for VZV.

2. Serotype and Strain Specificity of 93KA9 Antibody

The serotype of the 93KA9 antibody was determined by immunoassay using class-specific anti-human immunoglobulins. It was found that the 93KA9 antibody was of the IgG1,κ isotype.

The capacity of the antibody to bind different strains of VZV was tested by ELISA assay on virally infected cells. Binding of 93KA9 antibody was compared with that of pooled, human sera containing polyclonal anti-VZV antibodies. It was found that 93KA9 bound to all of the 11 clinical isolates and 1 laboratory strain of VZV tested. Moreover, the extent of binding of 93KA9 to the various strains correlated well with the extent of binding by the pooled sera. Since the pooled sera may be presumed to bind to the various strains approximately equally well, the 93KA9 antibody must also bind to the different strains about equally well.

3. Antigen Specificity

Immunoprecipitation was used to show that the 93KA9 antibody binds to the glycoprotein II (gpII) protein of VZV. First, a subconfluent human MRC-5 cell monolayer in a 150 $cm^2$ flask was infected with trypsinized VZV-infected MRC-5 cells in Eagle's MEM containing 2% FBS. After approximately 40 hours, when the cells exhibited about 50% CPE, the medium was replaced with glucose-free Dulbecco's MEM with 1% dialyzed FBS and 0.55 mM glucose (=10% of normal glucose concentration). The cells were held for 2 hours at 37° C. before adding 2 μCi/ml of $^{14}$C-glucosamine. After labelling for 20 hours at 37° C., the medium was removed and the flask rinsed 4 times with PBS. The cells, now at 90% CPE, were scraped off the plastic into cold detergent buffer (PBS with 1% deoxycholic acid, 1% NP-40 and 1% aprotinin). The harvested material was vortexed, freeze-thawed two cycles and sonicated for 30 seconds. The lysate was cleared at 12,000×g for 1 hour at 4° C. and stored at −70° C. until used.

For immunoprecipitation, 100 μl of lysate (containing about $10^5$ cpm) was mixed with 500 μl of 93KA9 antibody at 20 μg/ml (total 10 μg), or with control antibody, and incubated for 1 hour at 37° C. and then overnight at 4° C. 200 μL of a 10% suspension of *S. aureus* was added to each sample and incubated for 15 minutes and then centrifuged at 12000×g for 10 minutes at 4° C. After washing the pellets five times, they were dissolved in 0.063 M Tris-HCl, pH 6.8, 2% SDS, 10% glycerol, 5% mercaptoethanol and 0.002% bromphenol blue. Vortexed samples were heated to 100° C. for 3 minutes and then centrifuged at 12,000×g for 10 minutes at 4° C. The supernatants were analyzed on a 10% SDS-PAGE gel according to the method of Laemmli. The gel was fixed and silver-stained. After destaining, the gel was treated in a fluor solution (En$^3$Hance, NEN) for 1 hour, rinsed and dried. The film was exposed to the gel for 40 days at −70° C. The results are shown in FIG. 3.

The immunoprecipitation pattern of 93KA9 (lane 2 of FIG. 3), consisting of an intense band with molecular weight (MW) calculated by comparison to the markers of 60 kilodalton (kDa) and a lighter band or doublet with MW somewhat above 100 kDa is identical to the pattern previously reported for antibodies against the VZV gpII protein (see lane 2 of FIG. 6 of Montalvo and Grose (1987), *J. Virol.* 61:2877), establishing that 93KA9 is specific for gpII. Indeed, the observed molecular weights are in the ranges 57–66 kDa and 115–140 kDA reported in the scientific literature for the respective bands (see, Davison et al. (1986), *J. Virol.* 57:1195). Moreover, as positive control, the mouse antibody 3C7 with known specificity for gpII (Forghani et al. (1984), *J. Virol.* 52:55) produced the same pattern as 93KA9 (lane 1 of FIG. 3). As negative control, 93KA9 did not precipitate any proteins from cells infected with herpes simplex virus (HSV) instead of VZV (lane 4 of FIG. 3).

4. Neutralization activity

To determine the ability of 93KA9 to neutralize VZV, various dilutions of antibody were mixed with the K.McC. clinical strain of VZV virus (obtained by sonication of infected cells) in the presence or absence of active guinea pig complement. As described in detail below, after 20 minutes, the samples were then adsorbed to MRC-5 human primary fibroblast cells in a 96-well plate. For comparison, dilutions of pooled human immunoglobulin (Sandoglobulin) and of Varicella-zoster immune globulin, VZIG (Massachusetts Public Health Biologic Laboratories) were also used to neutralize the virus. Because conventional plaque assays (see, e.g., Grose et al. (1979), *J. Infectious Disease* 139:142), are difficult to perform with VZV, the read-out was extent of cytopathic effect (CPE), estimated by microscopic examination of the cells as 100% (total cell layer destruction), 75%, 50%, 25% or 0% (no visible CPE). According to this assay, the $IC_{50}$ of 93KA9 antibody was 0.06 µg/ml in either the presence or absence of complement, and the $IC_{100}$ was 0.25 µg/ml (FIG. 1). By contrast, in the absence of complement VZIG was about 1000-fold less potent than 93KA9 and Sandoglobulin was about 6000-fold less potent (Table 1). Similar neutralization results were obtained with the laboratory VZV strain Ellen.

In more detail, MRC-5 cells were seeded at $0.5 \times 10^6$ cells/plate in a 96-well tissue culture plate in Eagle's MEM with 5% FBS and allowed to grow to near-confluence. Dilutions of antibody or immunoglobulin were made in Eagle's MEM with 2% FBS. 30 µl of each dilution was placed in the wells of a 96 well U-bottomed plate, 30 µl of a dilution of guinea pig complement or of medium was added to each well, and 30 µL of a dilution of VZV virus (clinical strain K.McC.) was added to each well. The plate was incubated at 37° C. for exactly 20 minutes. The medium was aspirated from the MRC-5 plate, and all 90 µl of the antibody-virus mixture was transferred from each well of the U-bottom plate to a corresponding well of the MRC-5 plate. The latter plate was incubated overnight at 37° C. in a 5% $CO_2$ atmosphere. The next day 125 µl of medium was added to each well and the incubation continued at 37° C. until stable cytopathic effect (CPE) appeared in the plate, as read under an inverted microscope.

TABLE 1

Neutralization of VZV by Antibodies

| Antibody | Complement | $IC_{50}$(µg/ml) | Relative potency of 93KA9 |
|---|---|---|---|
| 93KA9 | + | 0.0625 | 1 |
|  | − | 0.0625 | 1 |
| VZIG | + | 30.0 | 480 |
|  | − | 60.0 | 960 |
| Sandoglobulin | + | 93.3 | 1493 |
|  | − | 373.1 | 5970 |

Figure 2:
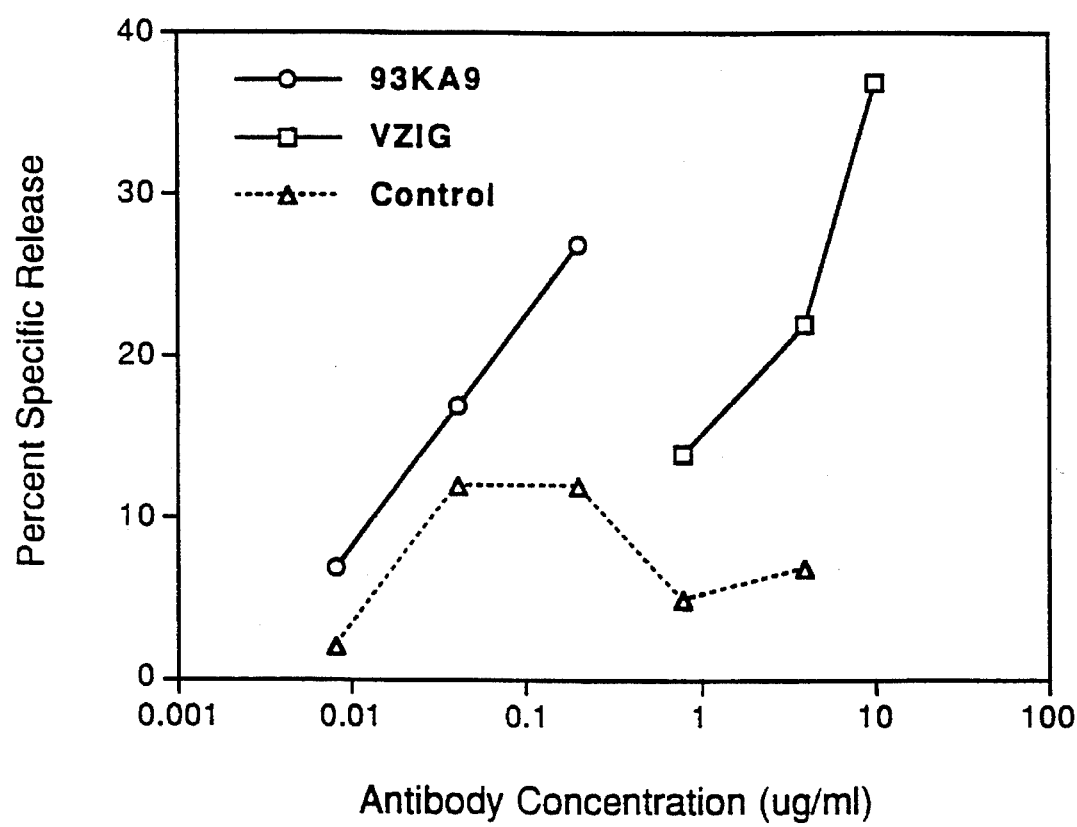
FIG. 2: Antibody dependent cellular cytotoxicity (ADCC) of VZV-infected MRC-5 cells by anti-VZV gpII human monoclonal antibody 93KA9, compared with pooled human sera and an unrelated human monoclonal antibody control.
Figure 3:
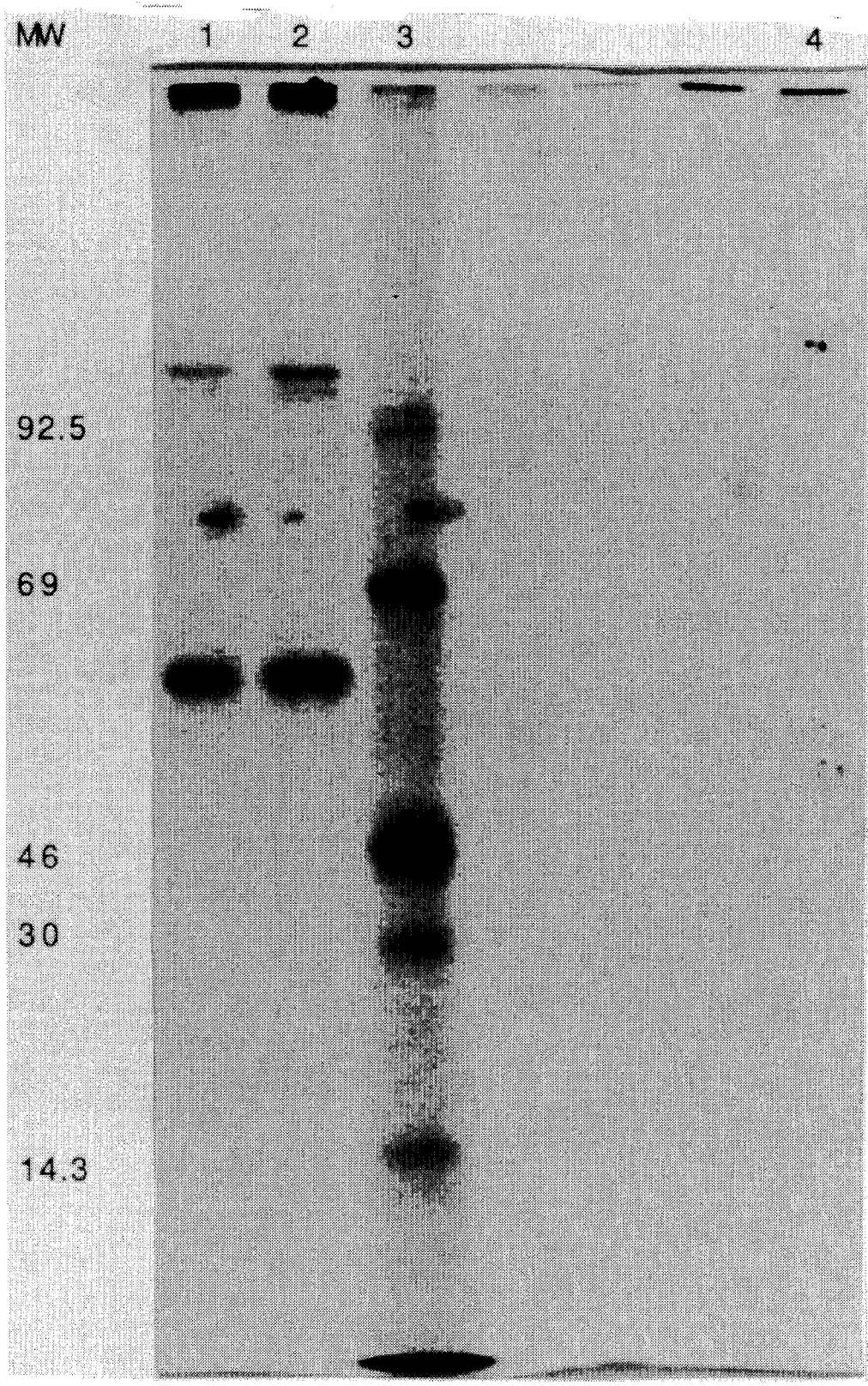
FIG. 3: SDS-PAGE gel analysis of immunoprecipitation of MRC-5 cells. Lane 1, VZV-infected MRC-5 cells precipitated with a mouse anti-gpII antibody; Lane 2, VZV-infected MRC-5 cells precipitated with 93KA9 antibody; Lane 3, Molecular weight standards, labeled at left side of gel in kilodaltons; Lane 4, HSV-infected MRC-5 cells precipitated with 93KA9 antibody.

5. Capacity of antibody 93KA9 to mediate antibody dependent cellular cytotoxicity 93KA9 antibody, VZIG pooled sera or an unrelated human control antibody was mixed with radiolabelled VZV-infected MRC-5 cells in the presence of human effector cells. ADCC was assayed by measuring radioactivity released by cell lysis. FIG. 2 shows that antibody 93KA9 was able to mediate ADCC at about a 100-fold lower concentration than VZIG.

6. Cloning of Light Chain and Heavy Chain cDNAs cDNA for the light and heavy chain variable region genes of the 93KA9 antibody were cloned using anchored polymerase chain reactions essentially as described (see Co et al. (1992), *J. Immunol.* 148:1149, which is incorporated herein by reference), using 3' primers that hybridized to human constant regions and contained HindIII sites, and 5' primers that hybridized to the dG tails and contained EcoRI and XbaI sites. The polymerase chain reaction (PCR) amplified fragments were digested with XbaI and HindIII (light chain) or EcoRI and HindIII (heavy chain) and cloned into the pUC18 vector for sequencing. At least two heavy chain (gamma-1) and two light chain (kappa) specific clones were sequenced. The gamma-1 clones and the kappa clones are respectively identical in sequence. The cDNA variable domain sequences and the deduced amino acid sequences are shown in FIG. 4.

The above examples are provided to illustrate the invention but not to limit its scope. Other variants of the invention will be readily apparent to one of ordinary skill and are encompassed by the claims of the invention. All publications, patents and patent applications cited in the application are hereby incorporated by reference for all purposes to the same extent as if each were individually denoted as being incorporated by reference.

What is claimed is:

1. A human monoclonal antibody, or a binding fragment thereof, that competes with human monoclonal antibody 93KA9 produced by the cell line deposited under the accession number HB 11549, for binding to Varicella-zoster virus and has a complement-independent neutralizing activity having an $IC_{50}$ of about 0.01–0.1 µg/ml.

2. The human monoclonal antibody or binding fragment of claim 1, wherein said complement-independent neutralizing activity has an $IC_{50}$ of about 0.06 µg/ml.

3. The human monoclonal antibody or binding fragment of claim 2, wherein said antibody exhibits antibody-dependent cellular cytotoxicity against cells infected with said virus.

4. The human monoclonal antibody or binding fragment of claim 3, wherein said antibody exhibits neutralizing activity against at least two strains of said virus.

5. The human monoclonal antibody of claim 1 that is 93KA9 produced by the cell line deposited under the accession number HB 11549.

6. The human monoclonal antibody of claim 1 comprising: a light chain variable region that comprises three complementarity determining regions as shown in FIG. 4A (SEQ. ID. NO. 2); and a heavy chain variable region that comprises three complementarity determining regions as shown in FIG. 4B (SEQ. ID. NO. 4).

7. The human monoclonal antibody of claim 1, comprising:

a mature light chain variable region having at least 85% sequence identity to the mature light chain variable sequence shown in FIG. 4A (SEQ. ID NO. 2); and a mature heavy chain variable region having at least 85% sequence identity to the mature heavy chain variable sequence shown in FIG. 4B (SEQ. ID. NO. 4).

8. A cell line capable of producing the human monoclonal antibody of claim 1.

9. The cell line of claim 8 that is HB 11549.

10. A recombinant DNA molecule comprising a DNA segment encoding a light or heavy chain variable region of the human monoclonal antibody of claim 1.

11. A recombinant DNA molecule of claim 10, wherein said human monoclonal antibody is 93KA9.

12. The recombinant DNA molecule of claim 10, wherein said light chain variable region has at least 85% sequence identity to the mature amino acid sequence shown in FIG. 4A (SEQ. ID NO. 2), and said heavy chain variable region has at least 85% sequence identity to the mature amino acid sequence shown in FIG. 4B (SEQ. ID NO. 4).

13. A cell line comprising:

a recombinant DNA segment encoding a heavy chain of a human monoclonal antibody that competes with monoclonal antibody 93KA9 for binding to Varicella-zoster virus; and a second recombinant DNA segment encoding a light chain of said human monoclonal antibody;

wherein said DNA segments are operably linked to first and second promoters and are capable of being expressed in said cell line wherein the antibody has a complement-independent neutralizing activity having an $IC_{50}$ of about 0.01–0.1 µg/ml].

14. The cell line of claim 13, wherein said human monoclonal antibody is 93KA9 produced by the cell line deposited under the accession number HB 11549.

15. The cell line of claim 14 that is a nonhuman mammalian cell line.

16. A human monoclonal antibody specific for Varicella-zoster virus which immunoprecipitates the gpII protein of Varicella-zoster virus from lysates of cells infected with said virus said protein of molecular weight on about 60 kilodaltons and a doublet protein of molecular weight greater than 100 kilodaltons as determined by SDS-PAGE and which neutralizes said virus with an $IC_{50}$ of about 0.06 µg/ml in the absence of complement.

* * * * *